United States Patent [19]
Jacob

[11] Patent Number: 5,882,327
[45] Date of Patent: Mar. 16, 1999

[54] LONG-TERM GLAUCOMA DRAINAGE IMPLANT

[76] Inventor: Jean T. Jacob, 3812 Ridgeway Dr., Metairie, La. 70002

[21] Appl. No.: 839,263

[22] Filed: Apr. 17, 1997

[51] Int. Cl.⁶ ..................................................... A61M 5/00
[52] U.S. Cl. ............................................... 604/8; 604/294
[58] Field of Search .................................. 604/294, 97, 8, 604/9, 10

[56] References Cited

U.S. PATENT DOCUMENTS

| | | |
|---|---|---|
| 4,457,757 | 7/1984 | Molteno . |
| 4,604,087 | 8/1986 | Joseph . |
| 4,634,418 | 1/1987 | Binder . |
| 4,750,901 | 6/1988 | Molteno . |
| 4,865,601 | 9/1989 | Caldwell et al. . |
| 4,932,968 | 6/1990 | Caldwell et al. . |
| 4,936,825 | 6/1990 | Ungerleider . |
| 4,946,436 | 8/1990 | Smith . |
| 4,955,909 | 9/1990 | Ersek et al. . |
| 5,178,604 | 1/1993 | Baerveldt et al. . |
| 5,192,315 | 3/1993 | Jacob-LaBarre . |
| 5,282,851 | 2/1994 | Jacob-LaBarre . |
| 5,338,291 | 8/1994 | Speckman et al. . |
| 5,372,577 | 12/1994 | Ungerleider . |
| 5,397,300 | 3/1995 | Baerveldt et al. . |
| 5,476,445 | 12/1995 | Baerveldt et al. . |

*Primary Examiner*—John G. Weiss
*Assistant Examiner*—Ki Yong O
*Attorney, Agent, or Firm*—Stephen R. Doody

[57] ABSTRACT

An implantable ocular device to decrease intraocular pressure by draining aqueous humor from the anterior chamber of the eye into an extraocular space above the sclera and below the conjunctiva and Tenon's layers. The device includes a conduit attached to an episcleral drainage plate having a porous posterior surface for cellular ingrowth and attachment by the sclera. The distal end of the conduit is inserted into the anterior chamber and protrudes out of the limbal/scleral junction. A portion of the outer surface of the conduit adjacent to the plate has a porous ingrowth surface area to enhance anchoring of the conduit to the surrounding extraocular tissues. The plate has a smooth anterior surface and a porous posterior surface. This device uses porous surfaces to enhance cellular infiltration and ingrowth to increase apposition with surrounding tissues, decrease micromovement of the implant, and thereby decrease the fibrous capsule formation surrounding the episcleral plate. Long-term failure of glaucoma drainage devices has been linked to thickening of the filtering bleb due to excessive fibrous capsule formation.

8 Claims, 6 Drawing Sheets

LONG-TERM GLAUCOMA DRAINAGE IMPLANT

FIELD AND BACKGROUND OF INVENTION

The present invention relates to a glaucoma drainage implant which allows fluid to filter out from the eye. One in 30 Americans over the age of 40 has some form of glaucoma. All types of glaucoma are characterized by an excessive accumulation of aqueous humor in the anterior chamber of the eye, which results in increased intraocular pressure, visual field loss, optic disc cupping, and when left untreated, blindness. To date, there is no known cure for any type of glaucoma.

Initially, medical therapy, i.e., topical medicine, is used to increase outflow and/or decrease production of aqueous humor. However, approximately, 40–50% of patients with glaucoma eventually fail medical therapy, and become candidates for complex forms of filtration surgery. These procedures, including full-thickness sclerectomy, trabeculectomy, and drainage implants, involve the making of a channel from the anterior chamber to the subTenon's space. The aqueous pool that accumulates under Tenon's layer forms a bleb from which the fluid is absorbed by the surrounding tissues.

One of the main reasons for the 10–50% failure rate of filtration surgery is inadequate reduction of intraocular pressure due to bleb failure (shunt closure) over either the short-term (weeks to months) or long-term (years) postoperative course. After the immediate postoperative period, the inability to maintain reduced intraocular pressure is the single most common serious complication of the three principal forms of filtration surgery mentioned above. Eyes with failed filtration surgery usually have no observable filtration bleb or have a thick-walled encapsulated bleb that is nearly impermeable. The bleb fails due to excessive healing characterized by fibroblastic proliferation and subconjunctival fibrosis. In eyes with inflammation, neovascularization, or previous intraocular surgery, this process of scarring is especially excessive.

Wound healing is a postinflammatory process that represents the effort of the body to repair and to restore the integrity and function of damaged tissue. The wound healing in response to filtration surgery is complicated by the presence of an activating factor (the aqueous humor) and, in the case of drainage implants, the presence of the implant itself. Encapsulation by a fibrous capsule is the normal wound healing response of the host to an implant and to the associated local trauma caused by the implantation process. The extent of the development of the fibrous capsule adjacent to a prosthetic implant is related to both the size and surface characteristics of the implant as well as to the degree of chemical inertness.

For implants in dynamic situations, such as vascular grafts, tendons, and patches on moving organs (heart, stomach, striated muscles, intestines), being smooth and inert is a hindrance to long term anchoring. Integration between the implant and the host is necessary to prevent detachment or shifting of the implant. Sutures are often inadequate for this purpose because simple tacking sutures allow the implant to shift and bulge. Suturing the entire length and circumference of the implant introduces the possibility of leakage of the internal organ fluid such as blood and bile through the suture holes and impairment of the strength of the implant. On the outside of the eye, porosity of the implant that allows integration of the host tissue would be very important in stabilizing the micro- movement of an implant in such a dynamic environment. Infiltration of tissue into the implant from the sclera would increase the apposition between the bottom surface of the implant and the upper surface of the sclera to an extent that neither sutures nor a fibrous capsule would be able to approximate.

Failed long-term drainage implants in human eyes have been shown to have dense fibrous capsules that ultimately cut off flow from the plate region. One reason for development of such a thick capsule around the implants is the chronic micromovement of the implant against the scleral surface, as discussed above. By designing a drainage device with porous cellular-attachment surfaces on the posterior plate surface and around the exterior surface of the tube, the device will be able to fix in place at the bleb site during the early healing period so that it will be sufficiently immobile as to offer little to no stimulus for further fibroblast activation.

The use of cellular attachment around or through the drainage device is a known means of improving the apposition between the device and the surrounding tissues. U.S. Pat. No. 5,338,291 to Speckman et al. uses texturing of the silicone surfaces of the drainage device plate to interrupt the formation of a dense fibrous capsule around the episcleral plate and to promote vascularization around said plate. The textured surface of Speckman's plate comprises a plurality of fingers extending generally uniformly and outwardly from the episcleral plate. The textured surfaces are used to cause an interruption of the fibrous capsule formation resulting in multi-planar collagen deposition. Additionally, U.S. Pat. No. 5,397,300 to Baerveldt et al. uses holes which extend through the plate to facilitate the formation of a tethered scar tissue bubble/bleb. It is intended that the scar tissue will grow through the hole or holes and pull the perimeter of the bubble/bleb towards the episcleral plate at the hole locations to tether the formation of the bleb through the plate to the scleral tissue.

However, the texturing system disclosed by Speckman has certain disadvantages. The cells and collagen of the fibrous capsule wrap around the perpendicular length of the projections but do not attach to them. Therefore the fibrous capsule response around the finger-like texturing only helps to immobilize the implant from side to side motion in the plane parallel to the sclera. There remains a small space between the texturing and the capsule which allows the implant to move perpendicular to the sclera in response to the dynamic movements of the eye, such as muscle movements to produce accommodation, and flexure of the sclera produced by blinking and intraocular pressure fluctuations. Thus the micromovement of the device is somewhat decreased but not eliminated with the texturing.

Also, Speckman teaches that the anterior surface of their device is textured in addition to the posterior surface to interrupt dense fibrous capsule formation and to promote vascularization around the plate. However, this will allow the fibrous capsule to form around the texturing points on the anterior surface as well as on the posterior surface. The area for the aqueous humor to flow over and spread (bleb space) is significantly decreased with the microtexturing and is almost completely eliminated when the fibrous capsule forms around the texturing.

The holes taught by Baerveldt have other types of disadvantages. The holes require that the cells grow through the thickness of the plate, generally one millimeter, isolating themselves from other cells. The circumferential size of the holes, particularly in view of the thickness of the plate and the smooth surface of the hole walls, present a very difficult surface area for the cells to try and attach to while growing. The overall effect of these parameters limit cellular ingrowth through the holes. Additionally, if sufficient holes are placed throughout the episcleral plate to facilitate the cellular ingrowth through them, then there would no longer be sufficient surface area on the anterior surface of the plate to disburse the aqueous humor flowing thereon, and the tethers of cellular tissue through the plate would act as physical barriers impeding the dispersion of the aqueous humor.

SUMMARY OF INVENTION

The present invention provides an aqueous humor drainage device to relieve the elevated intraocular pressure associated with glaucoma. The device consists of a flexible drainage conduit connected to a pliable episcleral drainage plate with porous cellular attachment areas around the proximal end of the conduit and the sides and posterior surface of the drainage plate. The anterior aspect of the drainage plate is smooth and acts as a basin for the aqueous humor. The device allows the natural healing response, i.e., the formation of a fibrous capsule, around the implant to improve the adhesion of the device to the sclera. Cellular infiltration and collagen deposition into the porous aspects of the device forms a tight junction between the device and the sclera, preventing movement of the device. The formation of the fibrous capsule includes cellular infiltration and collagen deposition into the porous areas on the conduit, which causes both the anterior and posterior tissues surrounding the drainage conduit to adhere to the circumference of the conduit. In addition to increasing the degree of immobilization, tacking the anterior tissues to the conduit by fibrous capsule tissue ingrowth also helps to limit the bleb size. This is important since abnormally large blebs can cause ocular motor problems. Therefore the movement of device and the ultimate thickness of the fibrous capsule surrounding the device is kept to a minimum by the device provided for herein.

The porous surfaces of the device can have a average pore size ranging from 15 to 95 microns with the preferred surface having a nominal pore size of 35 microns. The porous structure of the surfaces allows for cellular infiltration and collagen deposition through the pores and around the walls of the pores such that movement of the device is prevented not only from side to side but also perpendicularly to the scleral surface. The porous surfaces can be of the same elastomeric material from which the drainage conduit and episcleral plate are made or can be made from another type of elastomeric material which is capable of being chemically or physically mated to both structures.

DETAILED DESCRIPTION OF THE PREFERRED EMBODIMENT

Figure 1:
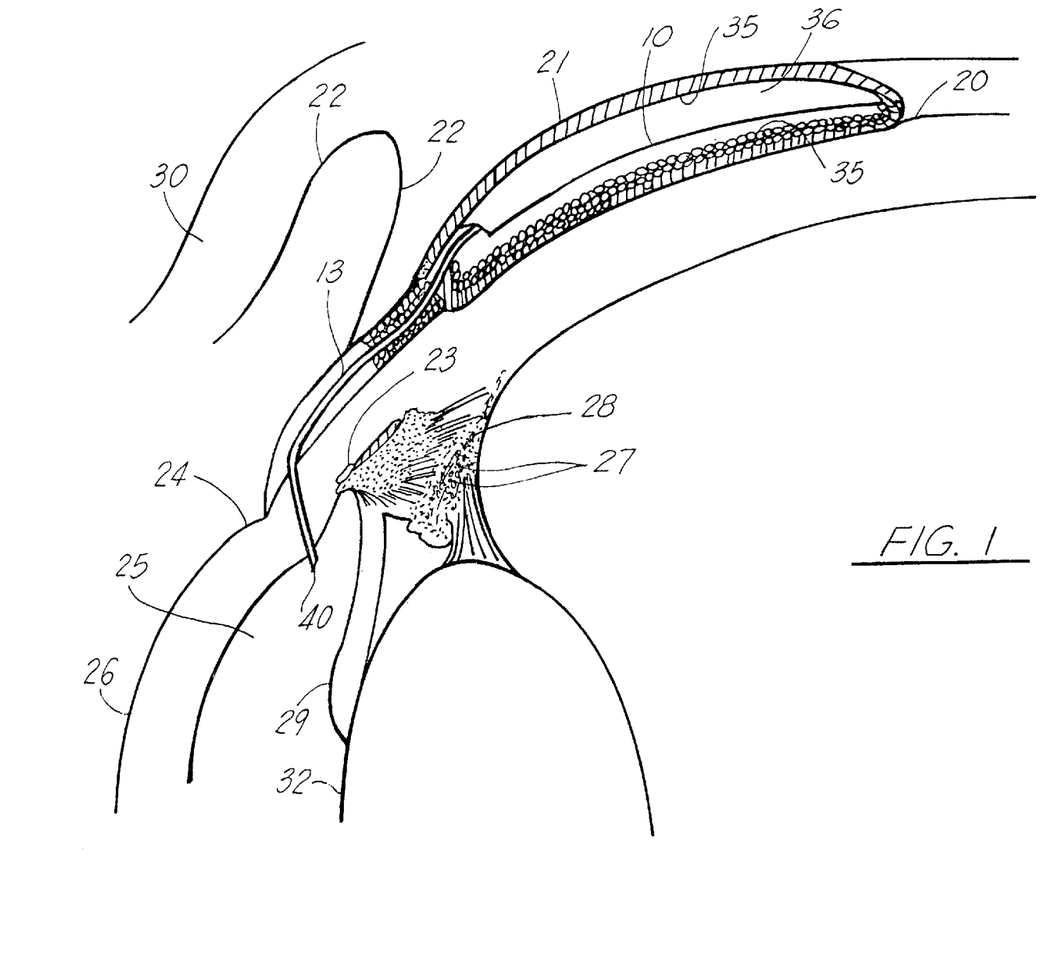
FIG. 1 is a partial sectional view of the eye showing the glaucoma drainage device of this invention implanted within the eye, extending from inside the anterior chamber to the external posterior portion of the globe, wherein an episcleral plate is surrounded by a fibrous capsule.
Figure 2:
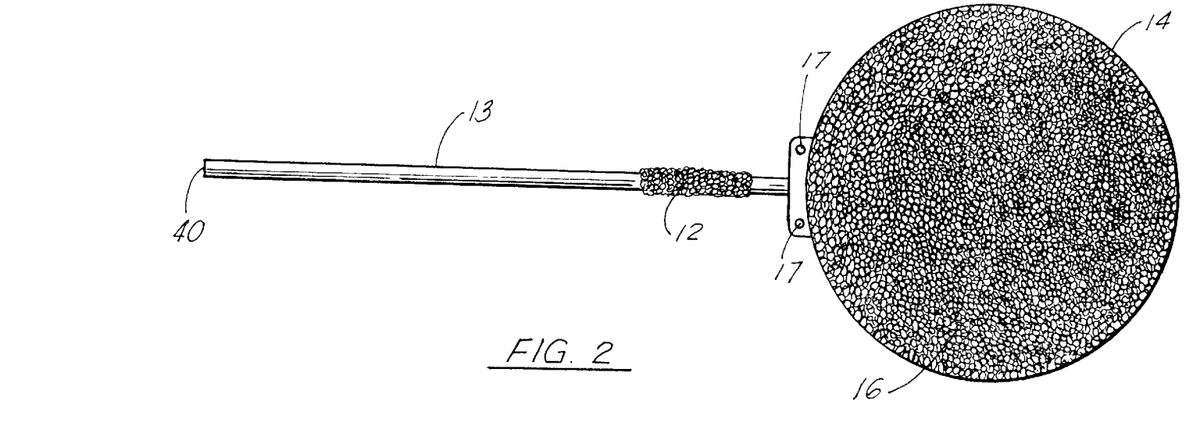
FIG. 2 is an enlarged bottom plane view of the glaucoma drainage device illustrated in FIG. 1.
Figure 3:
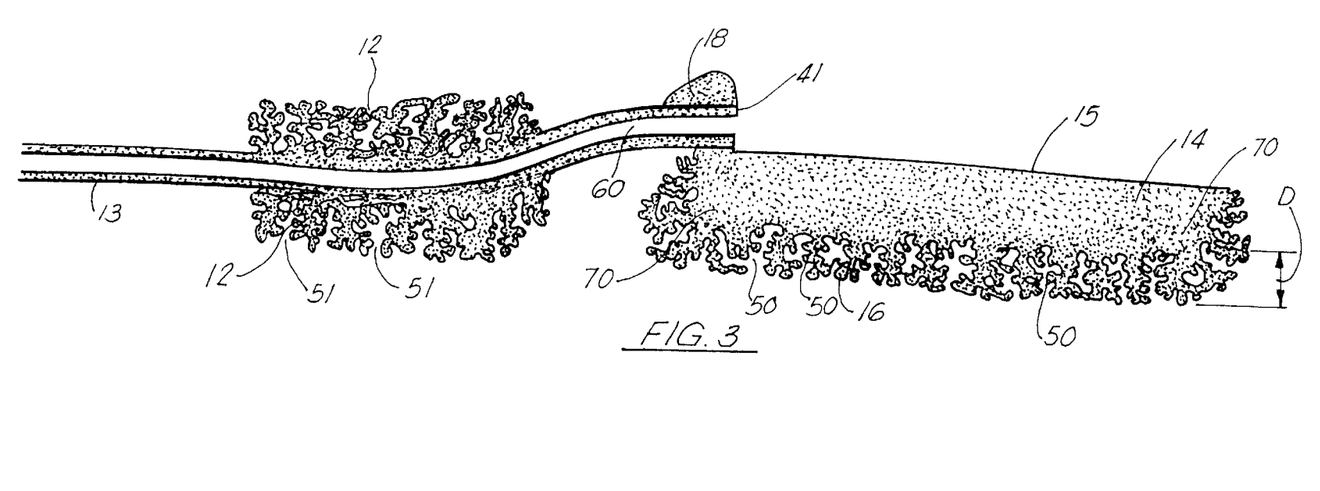
FIG. 3 is an enlarged, fragmented sectional view of the glaucoma drainage device illustrated in FIG. 1, taken along line 3—3 in FIG. 5.
Figure 4:
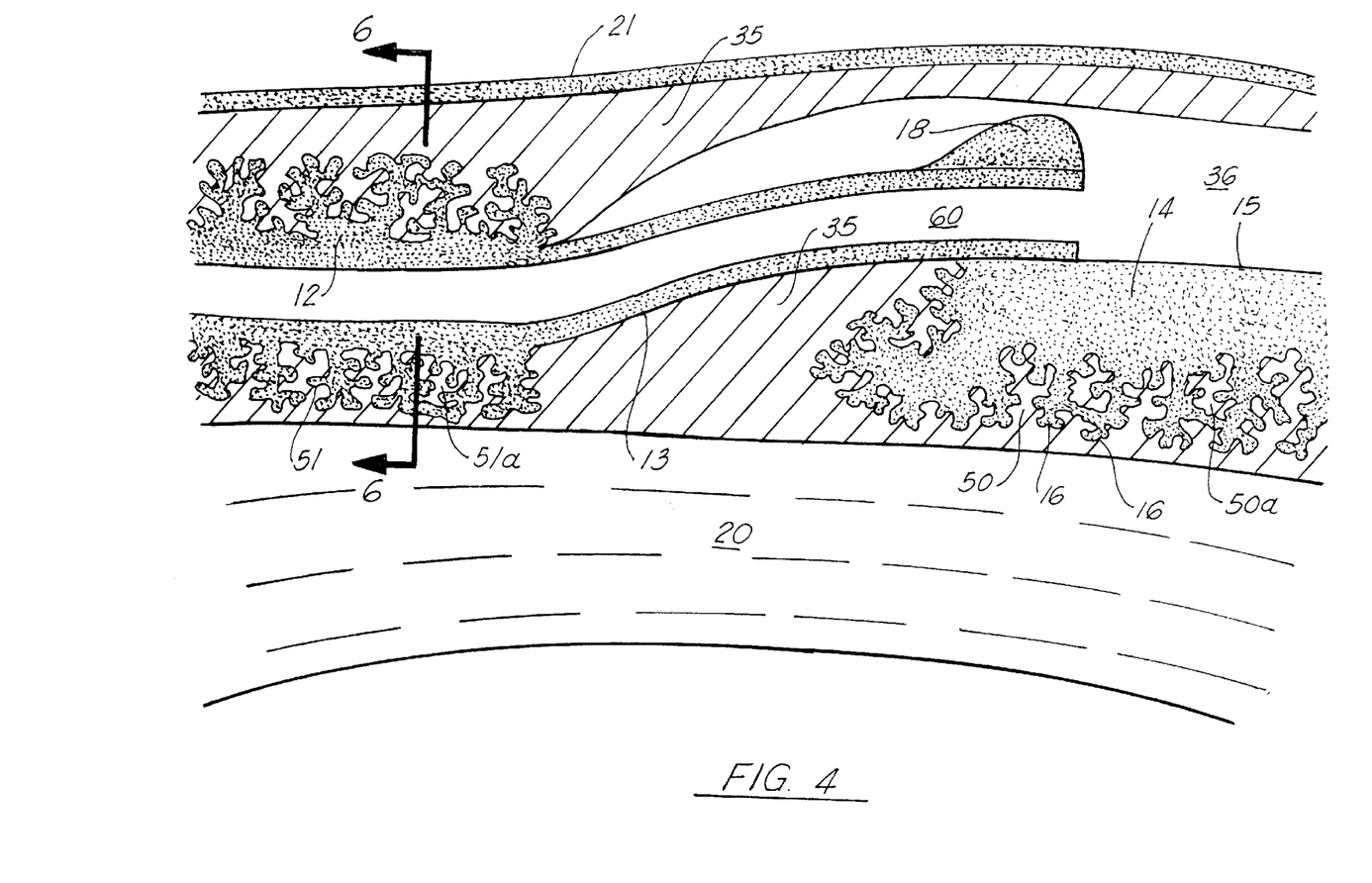
FIG. 4 is an enlarged partial view of the glaucoma drainage device illustrated in FIG. 3 showing the device implanted on the external posterior portion of the globe after the fibrous capsule has formed around it defining the bleb space.
Figure 5:
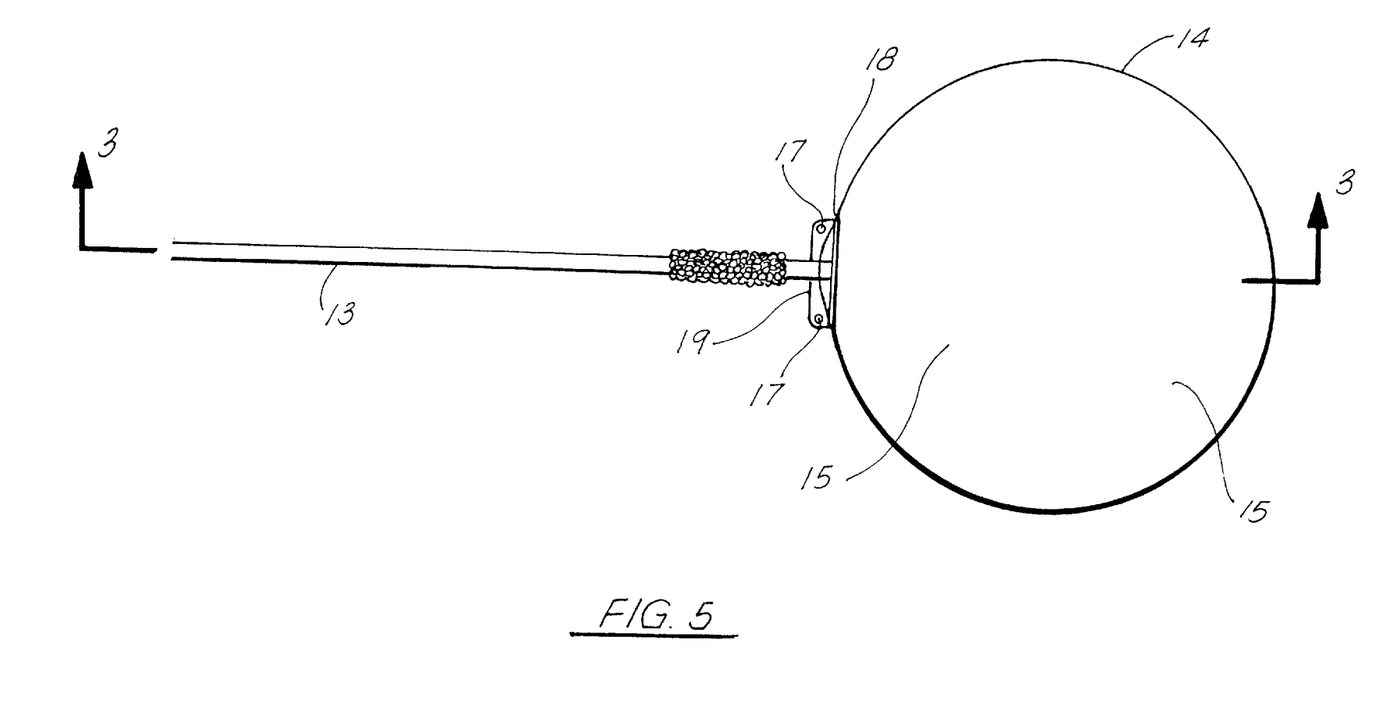
FIG. 5 is an enlarged top view of the glaucoma drainage device illustrated in FIG. 1.
Figure 6:
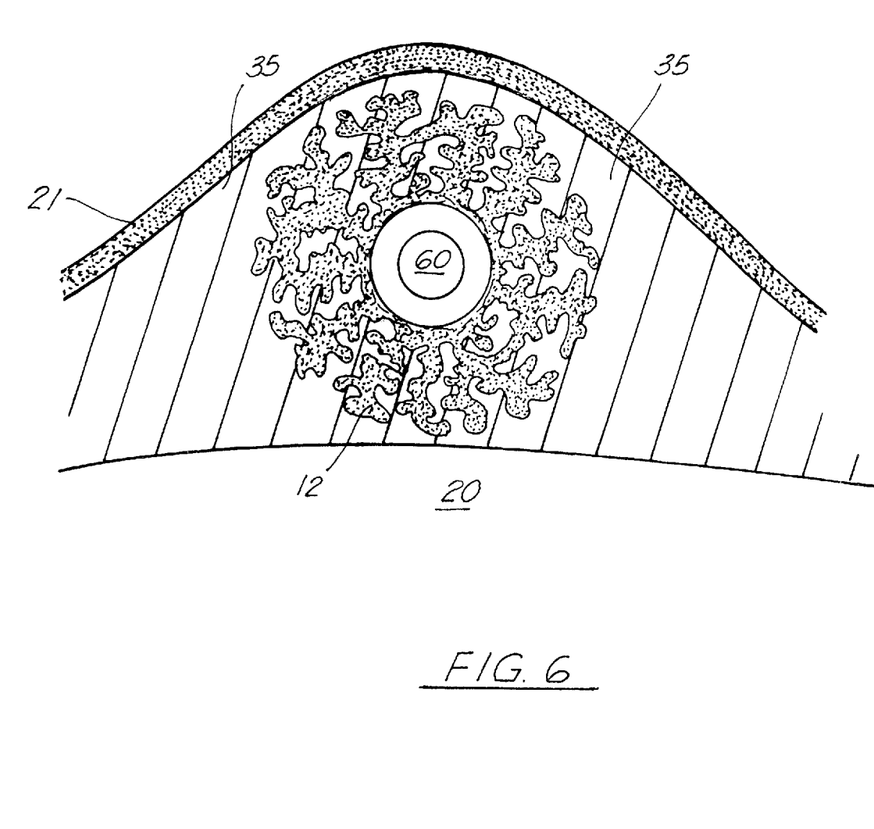
FIG. 6 is an enlarged cross-sectional view taken along line 6—6 in FIG. 4.

As shown in the drawings for the purpose of illustration, the present invention is an improved, long-term glaucoma drainage device, generally denoted by reference number 10, for surgical implantation in the eye 31 as depicted in FIGS. 1 and 4. The improved glaucoma drainage device 10 as illustrated in FIGS. 2 and 3 includes a drainage conduit 13 which is preferably flexible and tubular in shape. The distal end 40 of conduit 13 is free, as best shown in FIGS. 1, 2 and 5. The proximal end 41 of conduit 13 is attached to a drainage plate 14, as best shown in FIG. 3. The inner and outer surfaces of drainage conduit 13 are preferably smooth, with the exception of a portion of the outer surface of conduit 13 adjacent to its proximal end 41 which has a porous ingrowth surface 12, as best shown in FIGS. 2 and 3. Drainage plate 14 has a non-porous anterior surface 15 for aqueous fluid dispersement and a porous posterior surface 16 for cellular ingrowth and attachment to the scleral surface as shown in FIGS. 2, 3 and 4.

The drainage device 10 is implanted by a surgical procedure wherein the episcleral drainage plate 14 is attached to the external posterior surface of the sclera 20 of an eye 31, and the distal end 40 of conduit 13 is inserted into the anterior chamber 25 of the eye. FIG. 1 illustrates the device 10 implanted within the eye 31.

The relevant structures of the eye and some of their functions will be briefly described to provide an understanding of the present invention. The sclera 20 is the thick collagenous membrane which forms the outer walls of the almost ellipsoidal eye 31 except at the anterior central median where the thin optical membrane known as the cornea 26 forms a window into the eye. The sclera 20 deforms and responds to extraocular muscle movements and ocular pressure changes that occur during normal physiological functions of the eye. The junction where the cornea 26 and sclera 20 merge is referred to as the limbus 24. The conjunctiva 22 is a membrane of tissue which extends posteriorly from the limbus 24 over the front portion of the sclera 20 and then projects in a forward direction lining the upper and lower eyelids 30. Tenon's capsule 21 is a thin tissue membrane that attaches anteriorly at the limbus 24 beneath the conjunctiva 22 and extends posteriorly over the sclera 20 and extraocular muscles to attach at the back of the bony orbit within which the eye sits.

The ciliary body 28 begins internally in the eye at the limbus 24 and extends along the interior of the sclera 20. The iris 29, which extends radially into the center void of the eye from the anterior section of the ciliary body 28, forms the edges of the central space known as the pupil 32 and acts as a diaphragm controlling the size of the pupil. The anterior chamber 25 of the eye, which is bound anteriorly by the cornea 26 and posteriorly by the iris 29, is filled with a fluid produced primarily by the ciliary body 28, said fluid being referred to as the aqueous humor. The aqueous humor passes through the Trabecular meshwork 27 into the canal of Schlemm 23, and from Schlemm's canal the aqueous humor is subsequently drained into the veins leaving the eye 31.

The intraocular pressure of the eye is produced by the amount of aqueous humor within the eye at any time and, in a normal and healthy eye, is maintained at a constant level by natural bodily functions which balance the production and outflow of the aqueous humor. The disease state of glaucoma is most often characterized by an abnormally elevated intraocular pressure from either overproduction or decreased outflow of the aqueous humor. The present invention 10 is designed as a surgical intervention for uncontrolled glaucoma by facilitating the outflow of aqueous humor from the eye.

When surgically implanted, as shown in FIGS. 1 and 4, the drainage device 10 allows aqueous humor from the anterior chamber 25 to drain out of the eye through the drainage conduit 13 to the drainage plate 14 where it is dispersed through the filtration bleb 36 and then the fibrous capsule 35 that forms around the plate 14. The formation of fibrous capsule 35 around device 10 is a result of the natural wound-healing response to a foreign body or implant in the body that cannot be digested by macrophages, i.e., the implant is surrounded with a fibrous capsule to "wall" it if off from the rest of the body tissue. Fibrous capsule 35 formation first occurs in the range of 2 to 8 weeks post-implantation. It is the formation of the fibrous capsule 35 around the drainage plate 14 that eventually defines the space of the filtration bleb 36. FIGS. 1 and 4 specifically depict the position of the device after it has been implanted for several months, showing how the fibrous capsule 35 forms around not only the posterior portion and edges of drainage plate 14 but also anterior to the plate along Tenon's capsule 21.

Drainage plate 14, which is preferably pliable, is implanted beneath Tenon's capsule 21 so that the porous posterior surface 16 of drainage plate 14 is placed flush with the sclera 20. To facilitate the surgical implantation, drainage plate 14 is provided with flange 19 and suture holes 17 so that the plate can be anchored with sutures to the sclera 20. As implanted, drainage conduit 13 extends forward underneath Tenon's capsule 21 and the distal end 40 of drainage conduit 13 is inserted into the anterior chamber 25 through the sclera 20 just posterior of the limbus 24 and cornea 26. The porous ingrowth surface 12 of conduit 13 lays over the sclera 20 and the smooth portion of drainage conduit 13 extends into the anterior chamber 25 just anterior to the iris 29.

As illustrated in FIGS. 2, 3 and 5, drainage plate 14 is preferably circular or elliptical in general shape with an overall curvature and flexibility that allows it to conform to the curvature of the eye such that it may be implanted flush against the curved surface of the sclera. The plate 14 can be made from suitably pliable material such as elastomeric-type polymer materials like polysiloxane, polyurethane, polyethylene, polypropylene, polymethacrylate, polyacrylate and/or copolymers and/or derivatives thereof. The anterior surface 15 of plate 14 is preferably smooth and non-porous and may be treated with chemical moieties or be made of a polymer imparting a surface energy or sufficient degree of hydrophilicity to facilitate spreading of the aqueous fluid which flows out of conduit 13 and onto the anterior surface 15 of the plate.

The porous ingrowth posterior surface 16 of plate 14 can be made of the same material as the plate or another suitably porous material such as expanded polytetrafluoroethylene. The porous ingrowth surface 16 can be made as part of the plate in an injection molding process or can be fixed onto the plate with a suitable adhesive or bonding method. The porous ingrowth surface 16 preferably wraps around the side 70 of drainage plate 14, as shown best in FIG. 3. The porous ingrowth surface 16 preferably has a depth "D" of 0.35 mm to 1.25 mm, as shown in FIG. 3. The pores 50 of porous surface 16 can be irregular in shape, as shown in FIG. 4, having an average pore size in the range of 15 to 90 microns with the preferred surface having a nominal pore size of 35 microns. The preferred silicone embodiment of the device includes a porous silicone material, such as Interpore IP 100 made by Interpore International, Irvine, Calif., affixed to the edges and posterior portion of a silicone elastomer drainage plate with a medical grade silicone adhesive like Raumedic Adhesive (Rehau, Inc, Elk Grove Village, Ill.) to serve as porous surface 16.

As shown in FIGS. 4 & 5, plate 14 is preferably provided with a raised ridge 18 rising above the anterior surface 15 in the general area where the drainage conduit 13 is attached to the plate. A suitable opening is provided in raised ridge 18 to permit the proximal end 41 of conduit 13 to pass through ridge 18. The proximal end 41 of conduit 13 is attached to plate 14 by solvent, adhesive, heat or other suitable bonding. The purpose of the raised ridge 18 is to give stability to the bonding site and to prevent Tenon's and fibrous capsule tissue from clogging or blocking the lumen 60 of the drainage conduit 13.

Conduit 13, from its distal end 40 to its proximal end 41, is approximately 2–3 cms in length. Conduit 13 has a preferred inside diameter in the range of 0.011 to 0.015 inches and an overall outside diameter in the range of 0.020 to 0.035 inches, except for the portion of conduit 13 which has the porous ingrowth surface 12. The porous ingrowth surface 12 extends approximately 5–10 mms along the length of conduit 13. Pores 51 in ingrowth surface 12 have the same size range and preference as the pores 50 of porous surface 16.

Porous ingrowth surface 12 can be made out of the same material as conduit 13 or another polymer suitable for cellular ingrowth. Porous ingrowth surface 12 can be made as part of conduit 13, as in an injection molding process, or it can be fixed onto the conduit with a suitable adhesive or bonding method. Porous ingrowth surface 12 preferably has a depth of 0.30 mm to 3 mm, i.e., ingrowth surface 12 protrudes about 0.30 to 3 mm beyond the smooth outer surface of conduit 13. Porous ingrowth surface 12 is located adjacent to the proximal end 41 of conduit 13. Due to mechanical considerations, such as the adhesive attachment of porous ingrowth surface 12 to conduit 13, there may be a small length of conduit 13, between ingrowth surface 12 and the proximal end 41 of conduit 13, which is smooth as shown in FIG. 4. Alternatively, porous ingrowth surface 12 may extend along conduit 13 to the point where its proximal end 41 passes through raised ridge 18 of plate 14.

The interior surface of conduit 13 may be treated with chemical moieties or be made of a polymer imparting a surface energy or sufficient degree of hydrophilicity to facilitate the flow of aqueous fluid through the conduit. A preferred embodiment of conduit 13 is a silastic tubing such as silicone tube N5941 distributed by Storz Instrument Co, St. Louis, Mo. with Interpore IP100 (Interpore, Irvine, Calif.) wrapped and glued with medical grade silicone adhesive (Rehau, Inc, Elk Grove Village, Ill.) around the outer surface of the conduit to serve as ingrowth surface 12.

The shape and configuration of the pores 50 in porous surface 16 of plate 14 is similar to the shape and configuration of the pores 51 in ingrowth surface 12. The pores extend from the surface into the interior of the material. The pores can be continuous with each other and form a network in the material into which cells can migrate and deposit collagen within. The pores can be created by blowing gas through the polymer during manufacture, polymerizing a foam in place, weaving polymer strands, spin extruding/ casting polymer into a mesh, removing a soluble mold or salt from the cast polymer or other suitable methods. FIG. 4 gives a general representation of how porous ingrowth surface 12 and porous surface 16 have discrete openings, i.e., pores, and that the polymer forms the walls of said pores. Some of the pores may be partly encapsulated or enveloped by the polymer, as for example pores 50a and 51a as shown in FIG. 4, thereby creating porous "tunnels." Such porous tunnels, in the case of porous surface 16, do not extend all the way through plate 14 but instead loop back around such that the entrances and exits of said tunnels are located on the posterior surface of plate 14.

The formation of fibrous capsule 35 includes cellular infiltration and collagen deposition into pores 50 and 51, which facilitates and promotes adherence of the device 10 to the sclera 20. Hence, cellular ingrowth of the fibrous capsule into pores 50 and 51 securely anchors the implant in place and, unlike prior drainage implants, prevents any independent movement of the implant in any direction, whether parallel or perpendicular to the surface of the sclera. Hence, the implant responds to normal ocular physiological functions as part of the sclera and is not recognized by the body as an object independent of the sclera. Accordingly, ingrowth surface 12 and porous surface 16 have the effect of significantly decreasing, if not totally eliminating, micromovement of drainage device 10 relative to the sclera. This is important to the success of the implant because any micromovement of the implant can continue to activate the foreign-body response of the eye and increase the fibrous capsule thickness around the implant. Such increased fibrous capsule thickness is detrimental because it may cut off or significantly restrict the flow of aqueous humor from the plate.

Bleb function is dependent upon the dissipation of the aqueous fluid through the walls of the bleb 36 which are formed by the fibrous capsule 35. Prior to fibrous capsule formation, drainage of aqueous humor from the eye 31 through the device 10 is unrestricted and can result in dangerously low intraocular pressure or hypotony of the eye. There are several known ways to prevent such over-drainage of the eye prior to fibrous capsule formation. For example, sutures can be tied tightly around the drainage conduit as it lays over the sclera to close the lumen 60 of the conduit. As another example, a suture can be threaded through lumen 60 of the drainage conduit during implantation so that it plugs any flow through the conduit, with the free end of the suture passed inferiorly under the conjunctiva 22 and out at the inferonasal limbus and then sutured to the globe with interrupted sutures. For both of these methods, the sutures are removed several weeks after implantation. A third method forpreventing early postoperative hypotony after implantation is by fitting a biodegradable plug into the lumen 60 of the drainage conduit 13 adjacent to its proximal end 41. The biodegradable plug will dissolve slowly over time, losing its continuity or mass, eventually allowing aqueous humor to flow out of the conduit and onto the plate.

Figure 7:
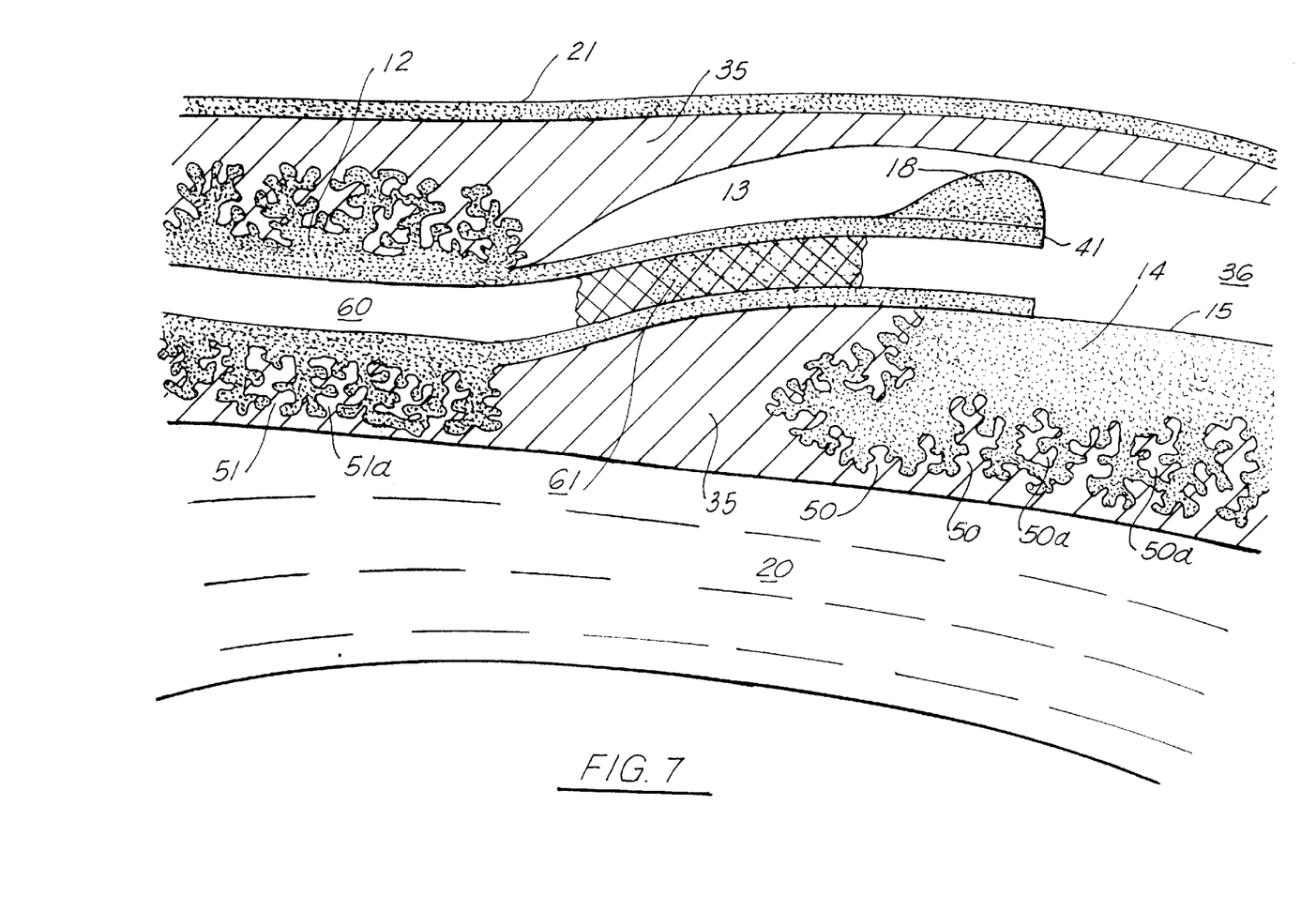
FIG. 7 is an alternative embodiment of the device illustrated in FIG. 4 which shows a plug located in the drainage conduit.

In an alternative embodiment of the present device 10, drainage conduit 13 may be provided with a drainage plug 61, as shown in FIG. 7, which contains drugs designed to prevent excessive fibrous capsule formation. Plug 61 is placed in the lumen 60 of the drainage conduit 13 as a drug delivery system. Drug is delivered to the tissues surrounding the bleb 36 slowly as the plug degrades and fluid flows from the anterior chamber. The plug 61 is made to fit snugly within the lumen 60 and is placed in the proximal end 41 of the conduit. In the preferred embodiment of the plug, the plug is hydrophilic in nature and swells within the conduit by imbibing the aqueous fluid that enters the conduit from the anterior chamber. The slight swelling of the plug 61 within the lumen 60 helps the plug 61 resist any intraocular pressure and maintain its position within the lumen 60 prior to dissolution/degradation. The drug within the plug 61 is concentrated in the center and proximal-most end of the plug to prevent possible flow of drug into the anterior chamber.

The drugs within the plug may include antiproliferative drugs, as for example 5-fluorouracil (5-FU), mitomycin C, bleomycin, taxol, daunorubicin and anthracyclines; drugs which affect collagen crosslinking, as for example beta-aminopropionitrile; drugs to increase fibrinolytic activity, as for example tissue plasminogen activator, and other suitable drugs. Such drugs can be entrapped in or hydrolyzably linked to the polymer chains of the biodegradable plug 61, which is preferably formed from a biodegradable or hydrolyzable polymer such as collagen, hyaluronic acid, chitin, chitosan, polylactic acids, polyglycolic acids, polyacrylates, polymethacrylates, polyacrylic acids, polyethylene glycols and/or suitable copolymers and/or derivatives thereof. As plug 61 dissolves, the drugs contained therein are released and delivered through conduit 13 onto plate 14 and ultimately to the tissues surrounding the bleb.

The device 10 is implanted in the eye 31 using standard ophthalmic procedures as described here briefly. The conjunctiva 22 and Tenon's capsule 21 are radially incised proximal to the limbus 24. The sclera bed 20 is exposed by blunt dissection of Tenon's capsule 21. The drainage plate 14 of the device is then sutured to the sclera 20 approximately 8 mm from the limbus 24. The anterior chamber 25 is entered with a small gauge needle, approximately 3 mm posterior to the limbus 24. The drainage conduit 13 is measured and cut so that its distal end 40 reaches the iridopupillary border when it is passed through the needle track and inserted into the anterior chamber 25. The conjunctiva 22—Tenon's 21 flap is re-approximated over plate 14 and conduit 13 and is sutured closed. The anterior chamber 25 is reformed with an air bubble injected at the limbus 24.

What is claimed is:

1. A surgically implantable drainage device to facilitate the flow of aqueous humor from an eye comprising a drainage plate having an anterior surface defining a drainage basin and having a porous posterior surface, wherein said porous posterior surface includes pores having a pore size of about 15 to 90 microns to promote cellular ingrowth and attachment of the device to the sclera of the eye, and a drainage conduit having a proximal end which is attached to and is in fluid communication with the drainage plate and a distal end which is capable of being inserted into the anterior chamber of the eye such that aqueous humor may flow from the anterior chamber of the eye, through the drainage conduit, and onto the drainage plate.

2. The device of claim 1 wherein said drainage conduit has a porous ingrowth surface to facilitate and promote adherence of the device to the sclera.

3. A surgically implantable drainage device to facilitate the flow of aqueous humor from an eye, comprising a drainage plate having a non-porous anterior surface defining a drainage basin and a posterior surface, wherein said posterior surface includes pores having a pore size of about 15 to 90 microns to promote cellular ingrowth and attachment of the device to the sclera of the eye; and a drainage conduit having a proximal end which is attached to the drainage plate and a distal end which is capable of being placed in the anterior chamber of the eye such that aqueous humor may flow from the anterior chamber of the eye, through the conduit, and onto the drainage plate.

4. The device of claim 3 wherein said drainage conduit has a porous ingrowth surface adjacent to its proximal end.

5. The device of claim 4 including a dissolvable drainage plug located in the conduit, and wherein said plug contains drugs which prevent excessive fibrous capsule formation, such that as the plug dissolves the drugs are released and delivered through the conduit, onto the plate and ultimately to the tissues of the eye which surround the bleb.

6. The device of claim 3 wherein the porous posterior surface of the plate wraps around the side of the plate.

7. The device of claim 3 wherein the porous posterior surface of the plate includes pores which are encapsulated so as to create porous tunnels having entrances and exits that are located on the posterior surface of the drainage plate.

8. A surgically implantable drainage device to facilitate the flow of aqueous humor from an eye comprising a pliable drainage plate having a smooth, non-porous anterior surface and a porous posterior surface for cellular ingrowth and attachment of the device to the sclera, a drainage conduit having a proximal end which is attached to the drainage plate and a distal end which is capable of being placed in the anterior chamber of the eye such that aqueous humor may flow from the anterior chamber of the eye, through the conduit, and onto the anterior surface of the plate, wherein said drainage conduit has a porous ingrowth surface adjacent to its proximal end for cellular ingrowth and attachment of the device to the sclera, wherein said drainage plate has a ridge rising above its anterior surface in the general area where the drainage conduit is attached to the plate, said ridge having an opening to permit the drainage conduit to pass therethrough, said ridge preventing fibrous capsule tissue from clogging the drainage conduit, and a dissolvable plug located in the drainage conduit, said plug containing drugs which prevent excess fibrous capsule formation, such that when said surgically implantable drainage device is in use and the plug dissolves, the drugs are released and delivered through the conduit, onto the plate and ultimately to the tissues of the eye which surround the bleb.

* * * * *